(12) United States Patent
Mordehai et al.

(10) Patent No.: US 9,455,132 B2
(45) Date of Patent: Sep. 27, 2016

(54) ION MOBILITY SPECTROMETRY-MASS SPECTROMETRY (IMS-MS) WITH IMPROVED ION TRANSMISSION AND IMS RESOLUTION

(71) Applicant: Agilent Technologies, Inc., Loveland, CO (US)

(72) Inventors: Alexander Mordehai, Loveland, CO (US); Layne Howard, Loveland, CO (US); Mark H. Werlich, Loveland, CO (US); Ruwan T. Kurulugama, Loveland, CO (US); Thomas A. Knotts, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/906,095

(22) Filed: May 30, 2013

(65) Prior Publication Data
US 2014/0353493 A1 Dec. 4, 2014

(51) Int. Cl.
*H01J 49/06* (2006.01)
*G01N 27/62* (2006.01)

(52) U.S. Cl.
CPC ........... *H01J 49/062* (2013.01); *G01N 27/622* (2013.01)

(58) Field of Classification Search
USPC .................................................. 250/287, 398
See application file for complete search history.

(56) References Cited

U.S. PATENT DOCUMENTS

| | | | |
|---|---|---|---|
| 3,639,757 A * | 2/1972 | Caroll et al. .................. | 250/282 |
| 7,064,322 B2 | 6/2006 | Crawford | |
| 7,829,841 B2 * | 11/2010 | Bateman .............. | G01N 27/622 250/281 |
| 7,838,826 B1 * | 11/2010 | Park ..................... | G01N 27/622 250/281 |
| 7,888,635 B2 | 2/2011 | Belov et al. | |
| 8,222,597 B2 * | 7/2012 | Kim et al. .................... | 250/292 |
| 2007/0158545 A1 * | 7/2007 | Verentchikov ........ | H01J 49/004 250/282 |
| 2011/0147575 A1 | 6/2011 | Mordehai | |
| 2012/0305759 A1 * | 12/2012 | Park .............................. | 250/282 |

* cited by examiner

*Primary Examiner* — Phillip A Johnston
*Assistant Examiner* — Hsien Tsai

(57) ABSTRACT

An interface for an ion mobility spectrometry-mass spectrometry (IMS-MS) system includes a first ion guide for receiving ions from an IMS drift cell, and a second ion guide for receiving ions from the first ion guide, and positioned in a chamber separate from the first ion guide. Electrodes of the second ion guide subject the ions to an axial DC electric field while the second ion guide is held at a lower pressure than the first ion guide. In some embodiments, the first ion guide may be an ion funnel and the second ion guide may be a linear multipole device.

20 Claims, 6 Drawing Sheets

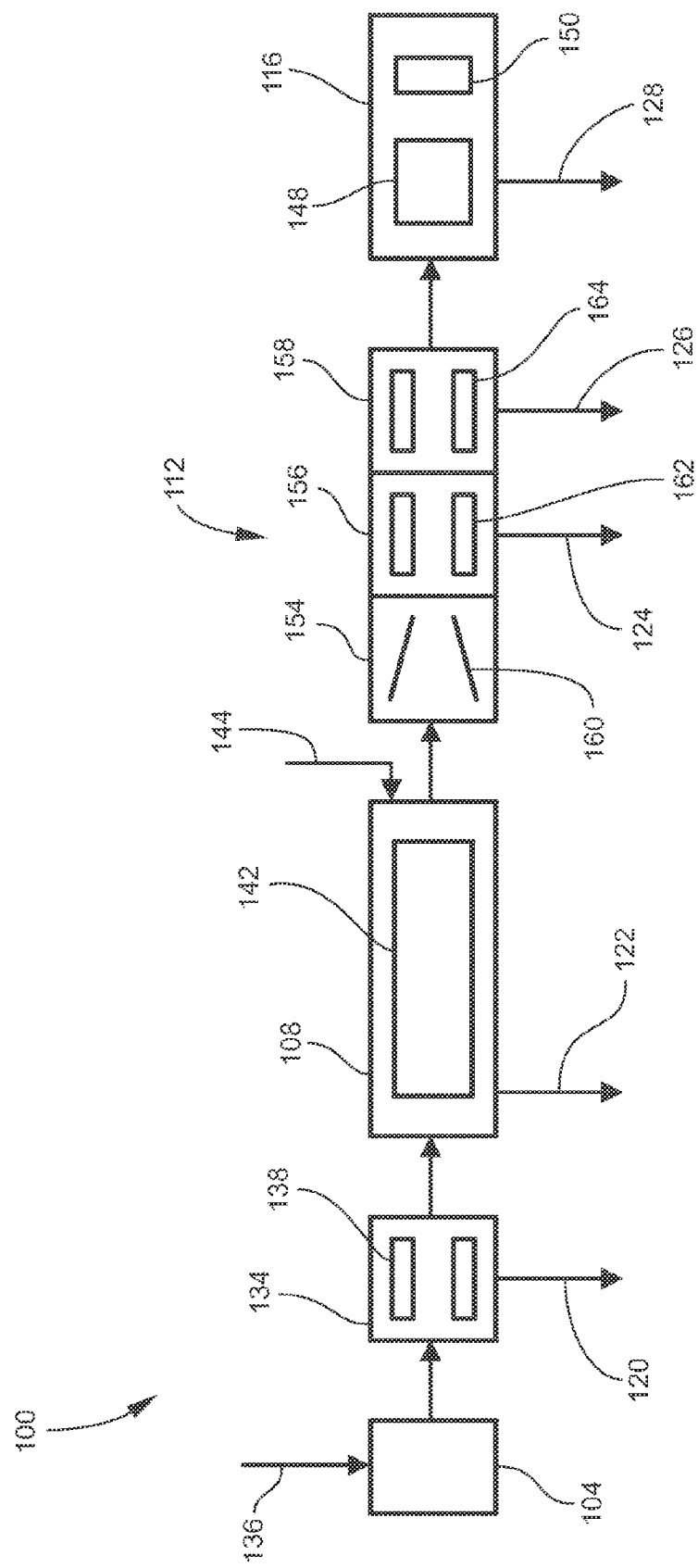

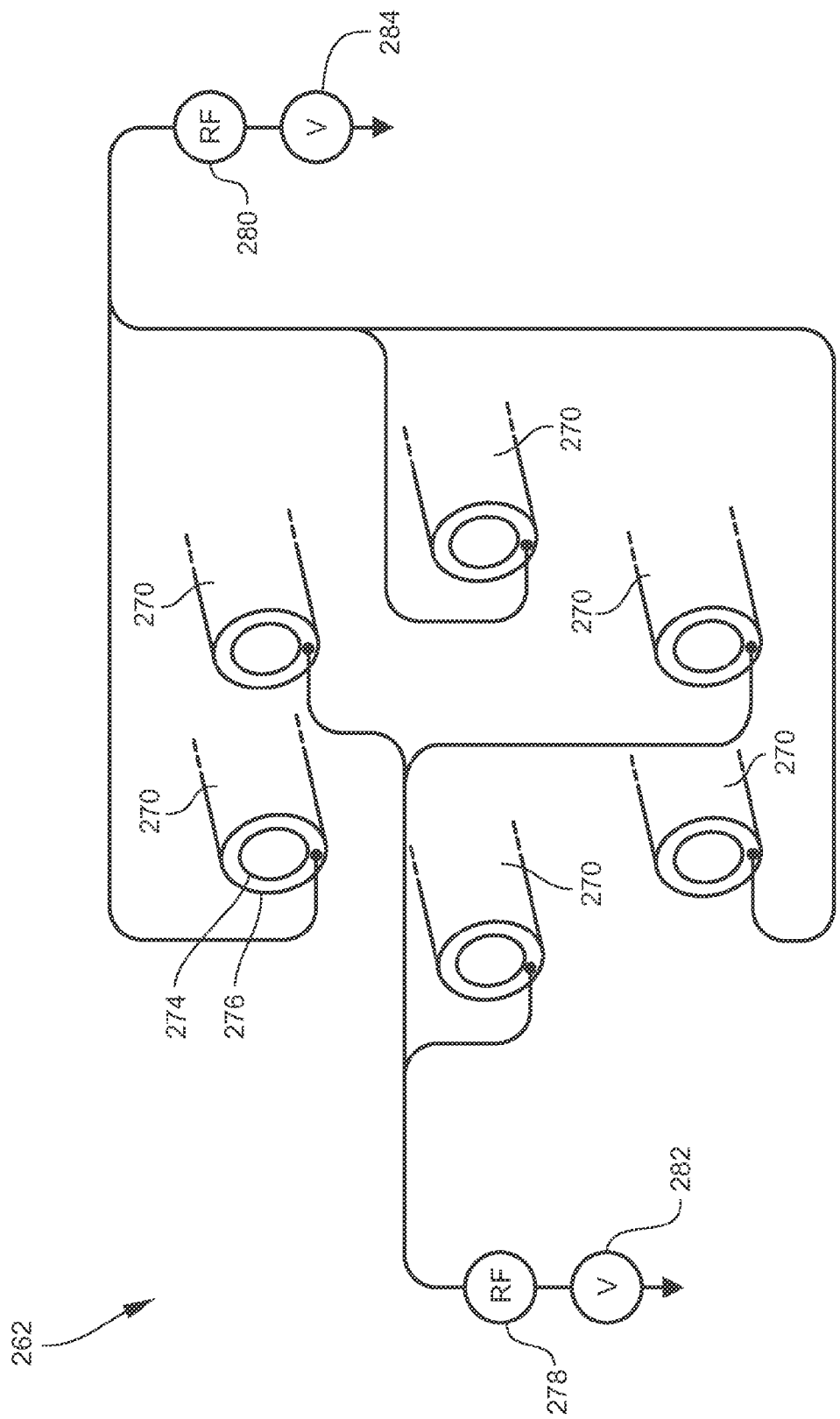

ION MOBILITY SPECTROMETRY-MASS SPECTROMETRY (IMS-MS) WITH IMPROVED ION TRANSMISSION AND IMS RESOLUTION

TECHNICAL FIELD

The present invention relates to coupling ion mobility spectrometry with mass spectrometry, and providing an interface between an ion mobility drift cell and a mass spectrometer.

BACKGROUND

Ion mobility spectrometry (IMS) is a fast, high-resolution gas-phase ion separation technique in which ions travel a known distance through a drift cell in an environment of a known gas pressure and composition. The ions are produced from a sample in an ion source and travel through the drift cell under the influence of a DC voltage gradient. During this travel, the ions become separated based on their different collision cross-sections, which can be correlated to their differing mobilities through the drift gas. From the drift cell the ions arrive at an ion detector that counts the separated ions, enabling the production of peak information useful for distinguishing among the different analyte ion species detected. An IMS system may be coupled online with a mass spectrometry (MS) system, which utilizes a mass analyzer to separate ions based on their differing mass-to-charge ratios (or m/z ratios, or more simply "masses"). In particular, an IMS system may be coupled with a time-of-flight (TOF) MS system that provides fast, high-resolution mass analysis. In the combined IMS-TOF MS system, ions are separated by mobility prior to being transmitted into the TOF MS where they are mass-resolved based on their flight times to the detector. Performing the two separation techniques in tandem is particularly useful in the analysis of complex chemical mixtures, including biopolymers such as polynucleotides, proteins, carbohydrates and the like, as the added dimension provided by the IM separation may help to mass-resolve large ions that are different from each other but present overlapping mass peaks. This two-dimensional separation technique may be further enhanced by coupling it with liquid chromatography (LC) techniques.

In known systems, IMS instrumentation has been coupled to TOF MS instrumentation by means of segmented quadrupole ion guides with multiple differentially pumped pressure regions, skimmer interfaces, and RF-only hexapole ion guides. These interface components can limit the IMS resolution and ion transmission across the mass range, and can also complicate the instrument design and manufacturing.

Therefore, there is a need for interfacing IMS instrumentation with TOF MS instrumentation in a way that optimizes IMS resolution and ion transmission.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, an interface for an ion mobility spectrometry-mass spectrometry (IMS-MS) system includes: a first ion guide configured for receiving ions from an IMS drift cell; and a second ion guide configured for receiving ions from the first ion guide and subjecting the ions to an axial DC electric field, the second ion guide positioned in a chamber separate from the first ion guide and communicating with a vacuum system wherein the second ion guide is at a lower pressure than the first ion guide.

According to another embodiment, an interface for an ion mobility spectrometry-mass spectrometry (IMS-MS) system includes: a housing comprising a first chamber and an adjacent second chamber fluidly isolated from the first chamber; an ion funnel in the first chamber, the ion funnel surrounding a funnel interior and configured for generating a radial RF ion confining field in the funnel interior; a multipole ion guide in the second chamber, the ion guide comprising a plurality of guide electrodes elongated along the axis, circumferentially spaced about the axis, and surrounding a guide interior, the guide electrodes configured for generating a radial RF ion confining field in the guide interior and an axial DC gradient along a length of the ion guide; and an ion lens element positioned on the axis between the ion funnel and the ion guide.

According to another embodiment, an ion mobility spectrometry-mass spectrometry (IMS-MS) system includes: an ion mobility spectrometer (IMS) comprising a drift cell exit; an IMS-MS interface, wherein an ion guide of the interface communicates with the drift cell exit; and a mass spectrometer (MS) positioned downstream of the interface.

According to another embodiment, a method for processing ions includes: separating ions in an ion mobility spectrometer (IMS) drift cell and transmitting the ions into a first ion guide; transmitting the ions into a second ion guide held at a lower pressure than the first ion guide; and transmitting the ions through the second ion guide by applying axial DC gradient along a length of the second ion guide while applying a two-dimensional RF field in the second ion guide.

According to another embodiment, a method for processing ions includes: transmitting an ion packet through an ion mobility spectrometer (IMS) drift cell to separate different ions of the ion packet based on mobility; transmitting the ions from the drift cell into an ion funnel; confining the ions to a beam along an axis of the ion funnel by applying a two-dimensional RF field in the ion funnel; transmitting the ions from the ion funnel into a multipole ion guide; transmitting the ions through the ion guide by applying axial DC gradient along a length of the ion guide while applying a two-dimensional RF field in the ion guide; and while transmitting the ions through the ion guide, maintaining the ion guide at a pressure lower than a pressure in the ion funnel.

According to another embodiment, an IMS-MS system is configured for performing any of the methods disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 1 is a schematic view of an example of an ion mobility spectrometry-mass spectrometry (IMS-MS) system according to some embodiments.

FIG. 2A is a perspective view of one end (entrance or exit) of an example of an interface ion guide according to some embodiments.

DETAILED DESCRIPTION

Figure 2B:
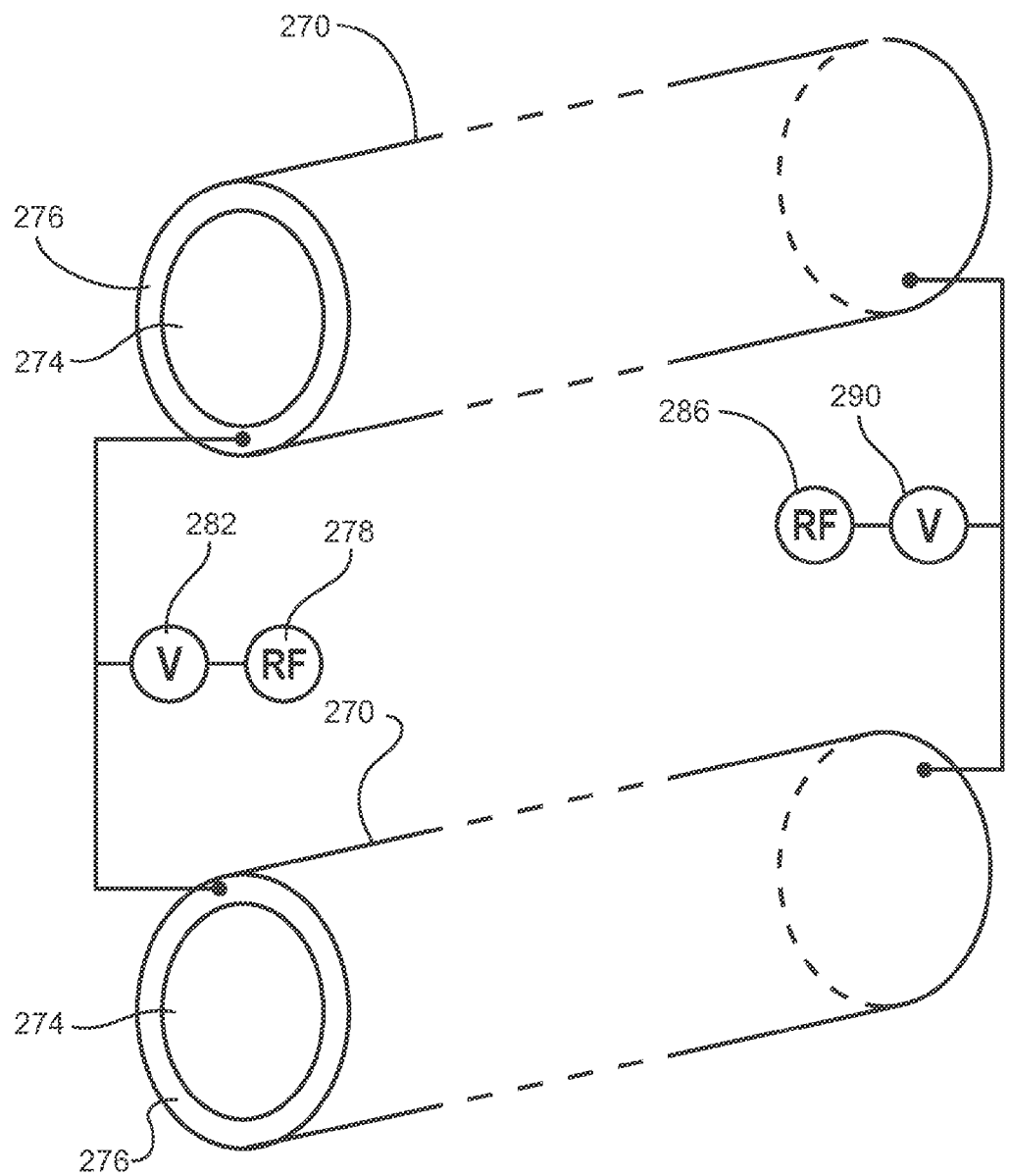
FIG. 2B is a perspective view of two guide electrodes of the ion guide illustrated in FIG. 2A.

FIG. 1 is a schematic view of an example of an ion mobility spectrometry-mass spectrometry (IMS-MS) system 100 according to some embodiments. The IMS-MS system 100 generally includes an ion source 104, an IMS 108, an IMS-MS interface 112, and an MS 116. The IMS 108 and IMS-MS interface 112 may be considered together as an IMS apparatus or assembly. The IMS-MS system 100 also includes a vacuum system for maintaining various interior regions of the IMS-MS system 100 at controlled, sub-atmospheric pressure levels. The vacuum system is schematically depicted by vacuum lines 120-128. The vacuum lines 120-128 are schematically representative of one or more vacuum-generating pumps and associated plumbing and other components appreciated by persons skilled in the art. The vacuum lines 120-128 may also remove any residual non-analytical neutral molecules from the ion path through the IMS-MS system 100. In practice, the IMS-MS system 100 may also include a system controller (not shown) for controlling various components of the IMS-MS system 100. The IMS-MS system 100 may also include an ion trap 134 between the ion source 104 and the IMS 108. In some embodiments in which the ion source 104 is configured for outputting pulses or packets of ions, the ion trap 134 may not be included. The operation and design of various components of IMS-MS systems are generally known to persons skilled in the art and thus need not be described in detail herein. Instead, certain components are briefly described to facilitate an understanding of the subject matter presently disclosed.

The ion source 104 may be any type of continuous-beam or pulsed ion source suitable for producing analyte ions for spectrometry. Examples of ion sources 104 include, but are not limited to, electrospray ionization (ESI) sources, other atmospheric pressure ionization (API) sources, photo-ionization (PI) sources, electron ionization (EI) sources, chemical ionization (CI) sources, field ionization (FI) sources, plasma or corona discharge sources, laser desorption ionization (LDI) sources, and matrix-assisted laser desorption ionization (MALDI) sources. In some embodiments, the ion source 104 may include two or more ionization devices, which may be of the same type or different type. Depending on the type of ionization implemented, the ion source 104 may reside in a vacuum chamber or may operate at or near atmospheric pressure. Sample material to be analyzed may be introduced to the ion source 104 by any suitable means, including hyphenated techniques in which the sample material is an output 136 of an analytical separation instrument such as, for example, a gas chromatography (GC) or liquid chromatography (LC) instrument (not shown).

The ion trap 134 generally includes a plurality of trap electrodes 138 enclosed in a chamber or housing. The chamber communicates with a pump that maintains the ion trap 134 at a pressure ranging from, for example, 1 to 10 Torr. The trap electrodes 138 are arranged about a trap axis and surround an interior region (trap interior) in which ions may be confined. The trap electrodes 138 are in signal communication with an appropriate voltage source, which includes a radio frequency (RF) voltage source and typically also a direct current (DC) voltage source. In response to applying an RF voltage of appropriate parameters (RF drive frequency and magnitude), and typically also a DC voltage of appropriate magnitude superposed on the RF voltage, the trap electrodes 138 are configured to generate a two-dimensional RF trapping field that confines ions of a desired mass range (m/z range) to the trap interior for a desired period of time. The ion trap 134 may be operated to accumulate ions and thereafter pulse the ions out to the IMS 108 in packets. In other embodiments, the trap electrodes 138 may be ring-shaped electrodes or plates with apertures that are axially spaced along the trap axis. In such embodiments, the trap electrodes 138 may be configured as an ion funnel with one or more converging cross-sections or both converging and diverging cross-sections.

The IMS 108 includes a drift cell 142 enclosed in a chamber. The chamber communicates with a pump that maintains the drift cell 142 at a drift gas pressure ranging from, for example, 1 to 10 Torr. A gas inlet 144 directs an inert drift gas (e.g., nitrogen) into the drift cell 142 chamber. The drift cell 142 includes a series of drift cell electrodes (typically ring-shaped) spaced along the axis. The drift cell electrodes are in signal communication with a voltage source to generate a DC voltage gradient along the axis. The axial DC voltage gradient moves the ions through the drift cell 142 against the flow of the drift gas, whereby the ions become separated in time based on their different cross-sections as appreciated by persons skilled in the art. The DC voltage gradient may be generated in a known manner, such as by applying a voltage between the first and last drift cell electrodes, and through a resistive divider network between the first and last drift cell electrodes, such that successively lower voltages are applied to the respective drift cell electrodes along the length of the drift cell 142.

The MS 116 may generally include a mass analyzer 148 and an ion detector 150 enclosed in a chamber. The vacuum line 128 maintains the interior of the mass analyzer 148 at very low (vacuum) pressure. In some embodiments, the mass analyzer 148 pressure ranges from $10^{-4}$ to $10^{-9}$ Torr. The mass analyzer 148 may be any device configured for separating, sorting or filtering analyte ions on the basis of their respective m/z ratios. Examples of mass analyzers include, but are not limited to, multipole electrode structures (e.g., quadrupole mass filters, ion traps, etc.), time-of-flight (TOF) analyzers, and ion cyclotron resonance (ICR) traps. The mass analyzer 148 may include a system of more than one mass analyzer, particularly when ion fragmentation analysis is desired. As examples, the mass analyzer 148 may be a tandem MS or MS$^n$ system, as appreciated by persons skilled in the art. As another example, the mass analyzer 148 may include a mass filter followed by a collision cell, which in turn is followed by a mass filter (e.g., a triple-quad or QQQ system) or a TOF analyzer (e.g., a qTOF system). The ion detector 150 may be any device configured for collecting and measuring the flux (or current) of mass-discriminated ions outputted from the mass analyzer 148. Examples of ion detectors 150 include, but are not limited to, electron multipliers, photomultipliers, and Faraday cups.

The IMS-MS interface 112 is configured for receiving the ions eluting from the drift cell 142 and transferring the ions to the MS 116 (or to intervening components between the drift cell 142 and the MS 116). The IMS-MS interface 112 includes a housing that includes a plurality of chambers, which may serve as pressure-reducing transitions between the IMS 142 and the MS 116. Each chamber may be fluidly isolated from the other chambers and provide an independently controlled pressure stage, while appropriately sized apertures are provided at the boundaries between adjacent chambers to define a pathway for ions to travel through the interface 112 from one chamber to the next chamber. As one non-limiting example, a front (or first) chamber 154 may be held at a pressure on the order of Torr, a middle (or second) chamber 156 adjacent to the front chamber 154 may be held at a pressure in a range from $1 \times 10^{-3}$ to $2 \times 10^{-1}$ Torr, and a rear (or third) chamber 158 may be held at a pressure in a range from $10^{-3}$ to $10^{-6}$ Torr. As another example, the middle chamber 156 may be held at a pressure 20 to 500 times lower than the front chamber 154, and the rear chamber 158 may be held at a pressure 20 to 500 times lower than the middle chamber 156. In some embodiments, the front chamber 154 may be part of (or an extension of, or in open communication with) the IMS chamber. The IMS-MS interface 112 also includes a plurality of "interface" ion guides enclosed in the respective chambers. In the present context, an "interface" ion guide is an ion guide configured for transmitting ions as a continuous beam without performing any type of mass selection, ion storage, or ion fragmentation. In any given chamber, the ion guide may be a linear multipole ion guide (typically, but not limited to, hexapole and octopole) or an ion funnel. Ion optics (not shown) may be provided between adjacent ion guides, and may form a part of the boundary between adjacent chambers.

In the illustrated embodiment, the front chamber 154 includes an ion funnel 160 and the middle chamber 156 and rear chamber 158 include respective multipole ion guides 162 and 164. The ion funnel 160 includes a plurality of axially spaced funnel electrodes surrounding a funnel interior that has a converging cross-section. The funnel electrodes are in signal communication with one or more RF and DC voltage sources. The funnel electrodes generate an RF (or composite RF/DC) ion confining field that constrains the radial component of the ion trajectories, thereby compressing the ions eluted from the drift cell 142 into a narrow beam along the funnel axis. The funnel electrodes also generate an axial DC voltage gradient to keep the ions moving toward and into the next ion guide and prevent ion stalling. The ion funnel 160 has a large ion acceptance and the geometry and size of the ion funnel entrance may be matched to the geometry and size of the drift cell exit. The ion funnel 160 may operate under similar fluid dynamic conditions as the drift cell 142, including gas flow rates and gas molecule concentrations. With the foregoing attributes, the ion funnel 160 may collect the ions eluting from the drift cell 142 with high efficiency (minimal loss of ions), and collect the full m/z range of eluted ions without mass discrimination. The ion funnel 160 may also transmit the full m/z range of ions as a focused beam into the next ion guide with high efficiency. The ion funnel 160 may perform these functions while preserving the ion mobility resolution and time coherence achieved in the drift cell 142.

The first multipole ion guide 162 (in the second chamber 156) includes a plurality of guide electrodes elongated along the axis, circumferentially spaced about the axis, and surrounding the guide interior. The number of ion guide electrodes may be 2N where N is an integer equal to 2 or greater. In typical embodiments, the guide electrodes are arranged in a hexapole or octopole configuration. Alternatively a quadrupole configuration may be sufficient, but at least for some applications a hexapole or higher-order configuration may be preferred due to lower voltage requirements and higher ion transmission efficiency. Multipole configurations of higher order than an octopole configuration may also be sufficient. The guide electrodes are in signal communication with one or more RF and DC voltage sources. The guide electrodes generate an RF (or composite RF/DC) ion confining field that keeps the ions focused in a beam along the guide axis. An axial DC voltage gradient is applied along the length of the first multipole ion guide 162 to keep the ions moving toward downstream components and prevent ion stalling. The DC voltage gradient may be applied between ion optics preceding and succeeding the guide electrodes, or may be applied to the guide electrodes as described by example below. The DC voltage gradient is applied while the pressure in the second chamber 156 is reduced to an intermediate value between that of the IMS 108 and that of the MS 116 (or an intervening component between the IMS 108 and the MS 116). The combination of the axial electric field and intermediate-level pressure reduction may preserve the IMS resolution and time coherence of the ion packets while allowing the ions to thermalize and avoiding undesired ion fragmentation.

In the present embodiment, a second multipole ion guide 164 is provided in a third chamber 158. The second multipole ion guide 164 includes a set of guide electrodes in signal communication with one or more RF and DC voltage sources. The second multipole ion guide electrodes may function similarly to the first multipole ion guide electrodes described above. The pressure in the third chamber 158 may be reduced to an intermediate value lower than that of the second chamber 156. As noted above, the pressure in the third chamber 158 may be very low such as on the order of $10^{-5}$ Torr. The very low pressure may greatly minimize the number of ion-neutral collisions occurring in this region, thereby improving ion transmission and preserving the IMS resolution.

It will be understood that FIG. 1 illustrates three interface chambers and respective ion guides by example only. More or less than three chambers and ion guides may be provided. Moreover, more than one ion guide may be provided in a given chamber.

FIG. 2A is a perspective view of one end (entrance or exit) of an example of an interface ion guide 262 according to some embodiments. FIG. 2B is a perspective view of two guide electrodes 270 of the ion guide 262. The ion guide 262 includes a set of axially elongated guide electrodes 270 (six in the illustrated example) circumferentially spaced about the guide axis. Each guide electrode 270 includes an electrically insulating element 274 (e.g., core) and an outer electrically resistive element 276 (e.g., layer or coating) surrounding the insulating element 274. The insulating element 274 may be composed of, for example, an insulating polymer, a ceramic, or an insulating oxide compound. The resistive element 276 may be composed of, for example, a resistive ink, a metallic oxide, a metal, a metal alloy, graphite, or a conductive polymer. The resistive element 276 may be fabricated as a layer exhibiting extremely uniform resistance to provide a substantially homogeneous axial DC voltage gradient along the length of all guide electrodes 270. The DC gradient may be generated by applying DC voltages to the opposing ends of the resistive element 276, instead of requiring the use of separate electrostatic lenses at the entrance and exit or separate electrode segments at the entrance and exit.

FIG. 2A schematically illustrates RF voltage sources 278 and 280 and DC voltage sources 282 and 284. The RF confining field is typically generated by applying an RF voltage of the same phase to alternating guide electrodes (to every other guide electrode, as one moves in a circle about the axis), with the RF phase on any given guide electrode being 180 degrees offset from the RF phase on the adjacent guide electrodes on either side of the given guide electrode. That is, the RF voltage applied to the first, third, and fifth guide electrodes is 180 degrees out of phase with the RF phase voltage applied to the second, fourth, and sixth guide electrodes. This configuration is depicted schematically by the first RF voltage source 278 placed in signal communication with the resistive elements 276 of the first, third, and fifth guide electrodes, and the second RF voltage source 280 placed in signal communication with the resistive elements 276 of the second, fourth, and sixth guide electrodes. In typical embodiments, the magnitude of the applied RF voltage is the same for all guide electrodes 270, and the magnitudes of the applied DC voltages is the same for all guide electrodes 270 at the either end.

Continuing with the present embodiment, FIG. 2B schematically illustrates RF voltage sources 278 and 286 and DC voltage sources 282 and 290 coupled to opposite ends of the guide electrodes 270 (only one pair of guide electrodes 270 being shown for simplicity). Typically, the RF voltages are applied uniformly along the length of each guide electrode 270 from end to end. Hence, schematically the RF voltage source 278 may be the same as the RF voltage source 286. The magnitude of the DC voltage 290 applied at the exit end of each guide electrode 270, however, may be different than the magnitude of the DC voltage 282 applied at the entrance end so as to generate an axial electric field gradient that accelerates the ions as described above.

In some embodiments, the guide electrodes 270 of the interface ion guide 262 may have structures and/or compositions as described in U.S. Pat. No. 7,064,322, the entire content of which is incorporated by reference herein.

Figure 3:
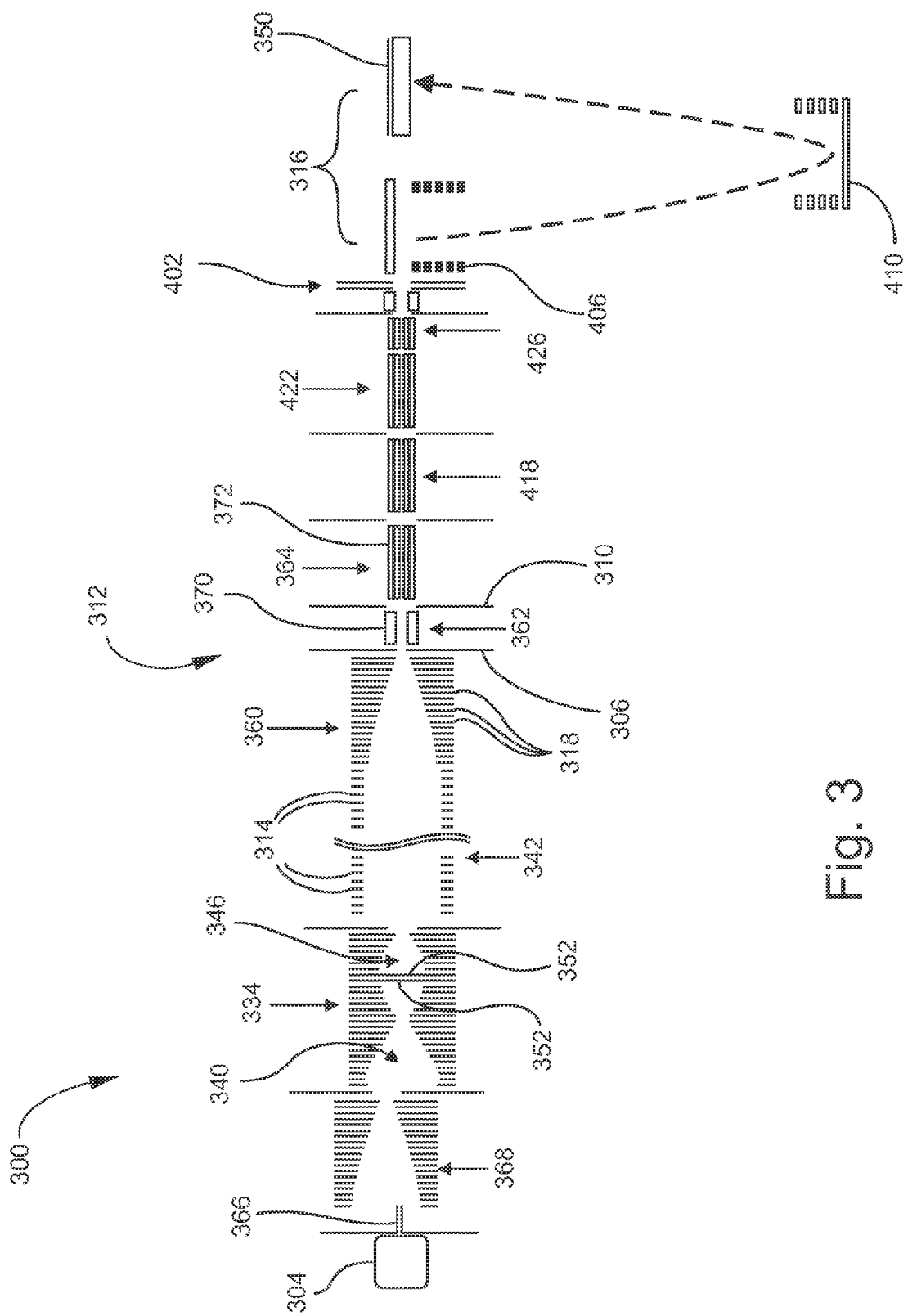
FIG. 3 is a schematic view of another example of an IMS-MS system according to some embodiments.

FIG. 3 is a schematic view of another example of an IMS-MS system 300 according to some embodiments. The IMS-MS system 300 includes an ion source 304, an accumulating/pulsing ion trap 334, an ion mobility drift cell 342, an IMS-MS interface 312, and an MS 316.

In the present example the IMS-MS interface 312 includes an ion funnel 360 immediately following the drift cell 342, a hexapole ion guide 362 following the ion funnel 360, and an octopole ion guide 364 following the hexapole ion guide 362. One or more electrostatic (DC-only) lens elements 306 and 310 are positioned between the ion funnel 360 and the hexapole ion guide 362, and between the hexapole ion guide 362 and the octopole ion guide 364. The drift cell 342 includes a plurality of drift cell electrodes 314 spaced along the longitudinal axis of the drift cell 342. The ion funnel 360 includes a plurality of axially spaced funnel electrodes 318, which apply RF and axial DC fields as described above. The hexapole ion guide 362 includes a plurality of axially elongated guide electrodes 370 circumferentially spaced about the axis, which apply RF and axial DC fields as described above. The octopole ion guide 364 includes a plurality of axially elongated guide electrodes 372 circumferentially spaced about the axis. The octopole ion guide 364 may be an RF-only device or may also apply an axial DC field in a manner analogous to the hexapole ion guide 362.

Figure 4:
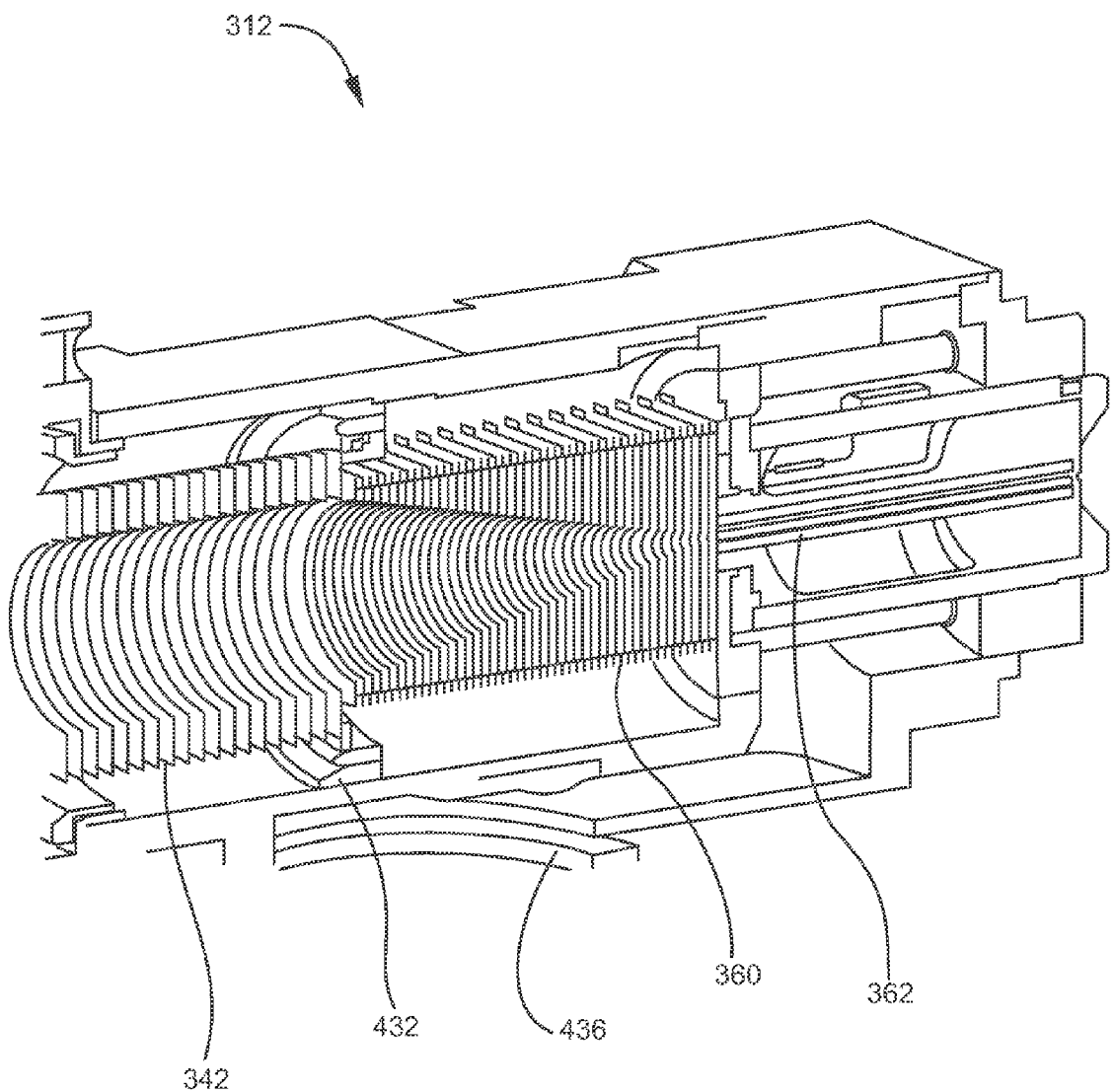
FIG. 4 is a cut-away perspective view of an IMS-MS interface of the IMS-MS system illustrated in FIG. 3.

FIG. 4 is a cut-away perspective view of the IMS-MS interface 312. A mounting member 432 in the interface housing positions the exit of the drift cell 342 and the inlet of the ion funnel 360 immediately adjacent to and aligned with each other. The hexapole ion guide 362 is positioned in a separate chamber and is evacuated via a vacuum port 436.

In one non-limiting example, the drift cell 342 may be 0.78 m in length, operate at a drift gas (e.g., nitrogen) pressure of about 4 Torr, and apply a drift field gradient of 20 V/cm. The hexapole ion guide 362 may be pumped down to about 30-40 mTorr. The octopole ion guide 364 may be pumped down to about $1 \times 10^{-5}$ Torr. The inside diameter of the conductance limiting aperture of the final ion funnel electrode 318 (the last electrode to which an RF voltage is applied) may be less than the inside diameter of the electrostatic lens element 306. For example, the inside diameter of the conductance limiting aperture may be 2.0 mm and the inside diameter of the electrostatic lens element 306 may be 3.0 mm. The electrostatic lens element 306 may be spaced at a distance of 0.7 mm from the hexapole ion guide 362. The other electrostatic lens element 310 may have an inside diameter of 2.5 mm, and may be spaced 0.7 mm from the hexapole ion guide 362 and 1.0 mm from the octopole ion guide 364.

In some embodiments the ion trap 334 may be provided in the form of an ion funnel, as illustrated in FIG. 3. The ion trap 334 may include a converging entrance region 340 and a diverging/constant-diameter/converging trap region 346. Electrostatic grid electrodes 352 in the trap region 346 may be utilized to pulse ions out to the drift cell 342. In some embodiments the interface between the ion source 304 and the ion trap 334 may include a transfer capillary 366 leading to a high-pressure ion funnel 368. As an example, the ion funnel 368 may operate at a pressure ranging from 2 to 30 Torr and the ion trap 334 may operate at a pressure ranging from 1 to 20 Torr. The ion funnel 368 may be oriented non-coaxially with the ion trap 334, with the axis of the ion funnel 368 being offset from (as illustrated) or at an angle to that of the ion trap 334. This configuration may be useful for reducing the amount of neutral species entering the trap region 346 and improving ion transmission into the trap region 346, as further described in U.S. Patent Application Publication No. 2011/0147575, the entire content of which is incorporated by reference herein.

In the illustrated embodiment, the MS 316 is a time-of-flight (TOF) MS with entrance optics 402, an ion extractor 406 (or pulser) and a flight tube (not shown) oriented orthogonally to the entrance optics 402, an ion detector 350, and an ion mirror 410 (or reflectron) to provide a 180° reflection in the ion flight path for extending the flight path and correcting the kinetic energy distribution of the ions. In some embodiments, the IMS-MS system 300 is configured as an IMS-QTOF system and thus may include a linear multipole (e.g., quadrupole) mass filter 418 for selecting ions and a collision cell 422 for producing fragment ions. The collision cell 422 typically has a linear multipole (e.g., hexapole) electrode configuration, and may be pressurized with a collision gas such as nitrogen to, for example, about 10 mTorr. Also in the present embodiment, an ion beam compressor 426 is positioned between the collision cell 422 and the TOF entrance optics 402 to provide efficient ion transmission. The region containing the entrance optics 402 may be pumped down to, for example, $1 \times 10^{-5}$ Torr.

Figure 5:
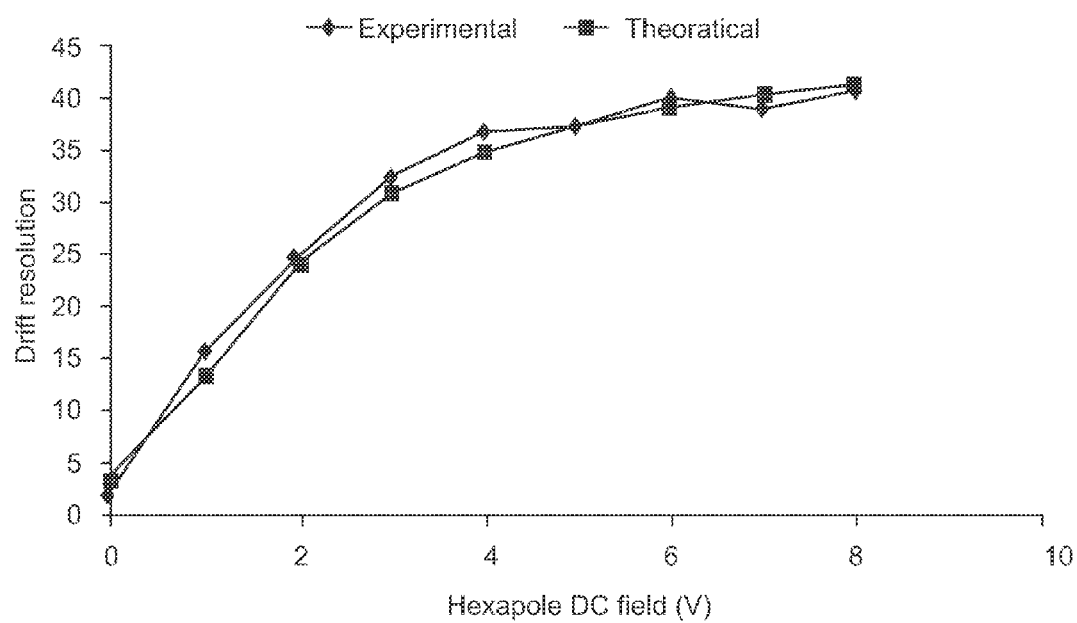
FIG. 5 is a plot of experimental and theoretical data demonstrating the dependence of the IMS drift resolution on the axial DC electric field applied across the interface ion guide.

The IMS-MS interface 312 shown in FIGS. 3 and 4 may provide the advantages described above in conjunction with FIG. 1, including improved IMS drift resolution and ion transmission. FIG. 5 is a plot of experimental and theoretical data demonstrating the dependence of the IMS drift resolution on the axial DC electric field applied across the interface ion guide 162 or 362. It is seen that the DC field may operate to maintain the optimum IMS resolution. The empirically derived theoretical IMS resolving power (R) as a function of the applied DC field is given by $R=A(1-[\exp(-B*V)])+C$, where the terms A, B and C are constants that depend on the ion of interest and V corresponds to the DC voltage applied across the interface ion guide 162 or 362.

Exemplary Embodiments

Exemplary embodiments provided in accordance with the presently disclosed subject matter include, but are not limited to, the following:

1. An interface for an ion mobility spectrometry-mass spectrometry (IMS-MS) system, the interface comprising: a housing comprising a first chamber and an adjacent second chamber fluidly isolated from the first chamber; an ion funnel in the first chamber, the ion funnel comprising a plurality of funnel electrodes serially positioned along an axis and surrounding a funnel interior, the funnel electrodes configured for generating a radial RF ion confining field in the funnel interior; a multipole ion guide in the second chamber, the ion guide comprising a plurality of guide electrodes elongated along the axis, circumferentially spaced about the axis, and surrounding a guide interior, the guide electrodes configured for generating a radial RF ion confining field in the guide interior and an axial DC gradient along a length of the ion guide; and an ion lens element positioned on the axis between the ion funnel and the ion guide.

2. The interface of embodiment 1, wherein the ion funnel comprises a funnel inlet, and further comprising a mounting member configured for positioning the funnel inlet and a drift cell in axial alignment with each other.

3. The interface of embodiment 1 or 2, comprising a vacuum system configured for maintaining the second chamber at a pressure lower than the first chamber.

4. The interface of embodiment 3, wherein the vacuum system is configured for maintaining the second chamber at a pressure 20 to 500 times lower than the first chamber.

5. The interface of embodiment 3, wherein the vacuum system is configured for maintaining the second chamber at a pressure in a range from $1\times10^{-3}$ to $2\times10^{-1}$ Torr.

6. The interface of any of embodiments 1-5, wherein the plurality of funnel electrodes comprises a front electrode, a rear electrode of lesser inside diameter than the front electrode, and a plurality of intermediate electrodes between the front electrode and the rear electrode, wherein at least a portion of the intermediate electrodes have successively reduced inside diameters.

7. The interface of any of embodiments 1-6, wherein the plurality of funnel electrodes comprises a rear electrode defining a funnel exit and having an inside diameter less than an inside diameter of the ion lens element.

8. The interface of any of embodiments 1-7, wherein the plurality of funnel electrodes comprises a rear electrode defining a funnel exit and having an inside diameter in a range from 1 to 5 mm.

9. The interface of any of embodiments 1-8, wherein each guide electrode comprises an insulating element and a uniform resistive element surrounding the insulating element.

10. The interface of embodiment 9, comprising a DC voltage source in signal communication with the resistive elements and configured for generating the axial DC gradient.

11. The interface of any of embodiments 1-10, wherein the number of ion guide electrodes is 2N where N is an integer equal to 2 or greater.

12. The interface of any of embodiments 1-11, wherein the number of ion guide electrodes is six or eight.

13. The interface of any of embodiments 1-12, wherein the ion guide in the second chamber is a first ion guide and the ion lens between the ion funnel and the ion guide is a first ion lens, and the housing further comprises a third chamber fluidly isolated from the second chamber, and further comprising: a second multipole ion guide in the third chamber; and a second lens element positioned on the axis between the first ion guide and the second ion guide.

14. The interface of embodiment 13, comprising a vacuum system configured for maintaining the third chamber at a pressure lower than the second chamber.

15. The interface of embodiment 14, wherein the vacuum system is configured for maintaining the third chamber at a pressure 20 to 500 times lower than the second chamber.

16. The interface of embodiment 14, wherein the vacuum system is configured for maintaining the third chamber at a pressure in a range from $10^{-3}$ to $10^{-6}$ Torr.

17. The interface of any of embodiments 13-16, wherein the second ion guide has a higher-order multipole configuration than the first ion guide.

18. The interface of any of embodiments 13-17, wherein the first ion guide has a hexapole configuration and the second ion guide has an octopole configuration.

19. An ion mobility spectrometry-mass spectrometry (IMS-MS) system, comprising: an ion mobility spectrometer (IMS) comprising a drift cell exit; the interface of any of embodiments 1-18, wherein the ion funnel communicates with the drift cell exit; and a mass spectrometer (MS) positioned downstream of the interface.

20. The IMS-MS system of embodiment 19, wherein the MS is a time-of-flight MS.

21. The IMS-MS system of embodiment 19 or 20, comprising an ion trap positioned upstream of the IMS.

22. The IMS-MS system of embodiment 21, wherein the ion trap comprises an ion funnel configuration.

23. The IMS-MS system of any of embodiments 19-22, comprising a front ion funnel positioned upstream of the IMS.

24. The IMS-MS system of any of embodiments 19-22, comprising a first front ion funnel and a second front ion funnel positioned upstream of the IMS, wherein the first front ion funnel is arranged along a first axis and the second front ion funnel is arranged along a second axis offset from or at an angle to the first axis.

25. The IMS-MS system of any of embodiments 19-24, comprising a collision cell between the interface and the MS.

26. The IMS-MS system of any of embodiments 19-24, comprising a mass filter and a collision cell between the interface and the MS.

27. A method for processing ions, the method comprising: transmitting an ion packet through an ion mobility spectrometer (IMS) drift cell to separate different ions of the ion packet based on mobility; transmitting the ions from the drift cell into an ion funnel; confining the ions to a beam along an axis of the ion funnel by applying a two-dimensional RF field in the ion funnel; transmitting the ions from the ion funnel into a multipole ion guide; transmitting the ions through the ion guide by applying axial DC gradient along a length of the ion guide while applying a two-dimensional RF field in the ion guide; and while transmitting the ions through the ion guide, maintaining the ion guide at a pressure lower than a pressure in the ion funnel.

28. The method of embodiment 27, comprising maintaining the pressure in the ion funnel in a range from 1 to 20 Torr.

29. The method of embodiment 27 or 28, comprising maintaining the pressure in the ion guide at a level 20 to 500 times lower than the pressure in the ion funnel.

30. The method of embodiment 27 or 28, comprising maintaining the pressure in the ion guide in a range from $1\times10^{-3}$ to $2\times10^{-1}$ Torr.

31. The method of any of embodiments 27-30, comprising transmitting the ions from the ion guide toward a mass spectrometer (MS), wherein the ion guide is maintained at a pressure higher than a pressure in the MS.

32. The method of embodiment 31, wherein the ion guide is maintained at a pressure two to three orders of magnitude higher than the pressure in the MS.

33. The method of any of embodiments 27-32, wherein the ion guide comprises a plurality of guide electrodes, each guide electrode comprising a conductive element, an insulating element surrounding the conductive element, and a resistive element surrounding the insulating element, and wherein the axial DC gradient is applied to the resistive elements.

34. The method of any of embodiments 27-33, comprising transmitting the ions through an electrostatic lens element between the ion funnel and the ion guide.

35. The method of any of embodiments 27-34, wherein the ion guide into which ions are transmitted from the ion funnel is a first ion guide, and further comprising: transmitting the ions from the first ion guide through a second ion guide; and while transmitting the ions through the second ion guide, maintaining the second ion guide at a pressure lower than the pressure in the first ion guide.

36. The method of embodiment 35, comprising maintaining the pressure in the second ion guide at a pressure 20 to 500 times lower than the pressure in the first ion guide.

37. The method of embodiment 35, comprising maintaining the pressure in the second ion guide in a range from $10^{-3}$ to $10^{-6}$ Torr.

It will be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. An interface for an ion mobility spectrometry-mass spectrometry (IMS-MS) system, the interface comprising:
    an ion mobility drift cell comprising a drift cell exit at which ions exit with a drift resolution;
    a housing comprising a first chamber, an adjacent second chamber fluidly isolated from the first chamber, and a third chamber downstream from the second chamber;
    an ion funnel in the first chamber communicating with the drift cell exit, the ion funnel surrounding a funnel interior and configured for generating a radial RF ion confining field in the funnel interior;
    a first multipole ion guide in the second chamber, the first multipole ion guide comprising a plurality of guide electrodes elongated along an axis, circumferentially spaced about the axis, and surrounding a guide interior, the guide electrodes each comprising an insulating element and a resistive element surrounding the insulating element, and the guide electrodes configured for generating a radial RF ion confining field in the guide interior and an axial DC gradient along a length of the first multipole ion guide configured for maintaining the drift resolution of the ions, wherein the first multipole ion guide is configured for operating at a pressure that avoids ion fragmentation;
    a second multipole ion guide in the third chamber; and
    an ion lens element positioned on the axis between the ion funnel and the first multipole ion guide.

2. The interface of claim 1, wherein the ion funnel comprises a funnel inlet, and further comprising a mounting member configured for positioning the funnel inlet and a drift cell in axial alignment with each other.

3. The interface of claim 1, comprising a vacuum system configured for maintaining the second chamber at a pressure lower than the first chamber.

4. The interface of claim 3, wherein the vacuum system is configured for maintaining the second chamber at a pressure 20 to 500 times lower than the first chamber.

5. The interface of claim 1, wherein the ion funnel comprises a funnel exit having an inside diameter less than an inside diameter of the ion lens element.

6. The interface of claim 1, wherein the resistive element is a uniform resistive element.

7. The interface of claim 6, comprising a DC voltage source in signal communication with the resistive elements and configured for generating the axial DC gradient.

8. The interface of claim 1, wherein the number of guide electrodes is 2N where N is an integer equal to 2 or greater.

9. The interface of claim 1, comprising a second lens element positioned on the axis between the first multipole ion guide and the second multipole ion guide.

10. The interface of claim 9, comprising a vacuum system configured for maintaining the third chamber at a pressure lower than the second chamber.

11. The interface of claim 10, wherein the vacuum system is configured for maintaining the third chamber at a pressure 20 to 500 times lower than the second chamber.

12. The interface of claim 9, wherein the second multipole ion guide has a higher-order multipole configuration than the first multipole ion guide.

13. An ion mobility spectrometry-mass spectrometry (IMS-MS) system, comprising:
   the interface of claim 1; and
   a mass spectrometer (MS) positioned downstream of the interface.

14. The IMS-MS system of claim 13, wherein the MS is a time-of-flight MS.

15. The IMS-MS system of claim 13, comprising an ion trap positioned upstream of the IMS.

16. A method for processing ions, the method comprising:
   transmitting an ion packet through an ion mobility spectrometer (IMS) drift cell to separate different ions of the ion packet based on mobility, wherein the ions exit the drift cell with a drift resolution;
   transmitting the ions from the drift cell into an ion funnel;
   confining the ions to a beam along an axis of the ion funnel by applying a two-dimensional RF field in the ion funnel;
   transmitting the ions from the ion funnel into a first multipole ion guide comprising a plurality of guide electrodes elongated along the axis;
   transmitting the ions through the first multipole ion guide by applying DC voltages to resistive elements of the guide electrodes to generate an axial DC gradient along a length of the first multipole ion guide while applying a two-dimensional RF field in the first multipole ion guide, wherein the axial DC gradient maintains the drift resolution of the ions;
   while transmitting the ions through the first multipole ion guide, maintaining the first multipole ion guide at a pressure lower than a pressure in the ion funnel; and
   transmitting the ions from the first multipole ion guide through a second multipole ion guide.

17. The method of claim 16, comprising maintaining the pressure in the first ion guide at a level 20 to 500 times lower than the pressure in the ion funnel.

18. The method of claim 16, wherein each guide electrode comprises an insulating element surrounded by the resistive element.

19. The method of claim 16, wherein each guide electrode comprises a conductive element, an insulating element surrounding the conductive element, and a resistive element surrounding the insulating element, and the axial DC gradient is applied to the resistive elements.

20. The method of claim 16, comprising, while transmitting the ions through the second multipole ion guide, maintaining the second multipole ion guide at a pressure lower than the pressure in the first multipole ion guide.

* * * * *